US009656028B2

(12) United States Patent
Leibovici

(10) Patent No.: US 9,656,028 B2
(45) Date of Patent: *May 23, 2017

(54) METHOD AND APPARATUS FOR APPLYING AN ANESTHETIC AND BATERICIDE

(71) Applicant: Jacob Leibovici, Wellington, FL (US)

(72) Inventor: Jacob Leibovici, Wellington, FL (US)

(73) Assignee: Leibovici LLC, Wellington, FL (US)

( * ) Notice: Subject to any disclaimer, the term of this patent is extended or adjusted under 35 U.S.C. 154(b) by 295 days.

This patent is subject to a terminal disclaimer.

(21) Appl. No.: 14/453,475

(22) Filed: Aug. 6, 2014

(65) Prior Publication Data

US 2015/0094661 A1 Apr. 2, 2015

Related U.S. Application Data

(63) Continuation-in-part of application No. 13/927,454, filed on Jun. 26, 2013, now Pat. No. 9,561,334, and a continuation-in-part of application No. 12/557,753, filed on Sep. 11, 2009, now Pat. No. 8,500,678, and a continuation-in-part of application No. 11/636,859, filed on Dec. 11, 2006, now abandoned.

(60) Provisional application No. 60/733,757, filed on Mar. 7, 2006.

(51) Int. Cl.

| | |
|---|---|
| ***A61M 5/32*** | (2006.01) |
| ***A61M 5/42*** | (2006.01) |
| ***A61M 5/31*** | (2006.01) |

(52) U.S. Cl.

CPC .......... *A61M 5/422* (2013.01); *A61M 5/3137* (2013.01); *A61M 2005/3139* (2013.01)

(58) Field of Classification Search

CPC .. A61M 2005/1787; A61M 2005/2414; A61M 2205/3606; A61M 5/19; A61M 5/24; A61M 5/422; A61M 35/003

See application file for complete search history.

(56) References Cited

U.S. PATENT DOCUMENTS

| | | | |
|---|---|---|---|
| 2,746,264 | A | 5/1956 | Keyes |
| 3,399,675 | A | 9/1968 | Hill |
| 3,483,869 | A | 12/1969 | Hayhurst |
| 3,563,239 | A | 2/1971 | Hill |
| 3,605,742 | A | 9/1971 | Tibbs |
| 3,971,375 | A | 7/1976 | Hill |

(Continued)

FOREIGN PATENT DOCUMENTS

| | | |
|---|---|---|
| EP | 2705866 | 3/2014 |
| JP | 08173531 | 7/1996 |

(Continued)

*Primary Examiner* — Rebecca E Eisenberg

(74) *Attorney, Agent, or Firm* — McHale & Slavin, P.A.

(57) ABSTRACT

A method and an apparatus for applying an anesthetic includes a receptacle having an upper end, a substantially hollow interior, a lower end having a tube or nozzle extending therefrom and an attachment for attaching to the barrel of a syringe or vice versa. The receptacle receives a container or canister containing an endothermic gas or vapor (propellant) that rapidly absorbs heat when released to the atmosphere. A depressible actuating member or trigger propels the gas or vapor through an outlet nozzle that is oriented to project a stream of gas or vapor along a delivery axis that intersects a delivery axis of the needle; therefore, the gas or vapor can be successively delivered to an injection site with minimal repositioning of the housing.

7 Claims, 18 Drawing Sheets

(56) References Cited

U.S. PATENT DOCUMENTS

| | | | |
|---|---|---|---|
| 4,109,653 | A | 8/1978 | Kozam et al. |
| 4,323,066 | A | 4/1982 | Bourdon |
| 4,430,079 | A | 2/1984 | Thill |
| 4,560,351 | A | 12/1985 | Osborne |
| 4,581,022 | A | 4/1986 | Leonard et al. |
| 4,725,265 | A | 2/1988 | Salrenji |
| 4,747,824 | A | 5/1988 | Spinello |
| 4,799,926 | A | 1/1989 | Haber |
| 5,180,371 | A | 1/1993 | Spinello |
| 5,190,521 | A | 3/1993 | Hubbard et al. |
| 5,236,419 | A | 8/1993 | Seney |
| 5,478,315 | A | 12/1995 | Brothers et al. |
| 5,603,695 | A | 2/1997 | Erickson |
| 5,690,618 | A | 11/1997 | Smith et al. |
| 6,139,529 | A | 10/2000 | Junior |
| 6,312,412 | B1 | 11/2001 | Saied et al. |
| 6,428,517 | B1 | 8/2002 | Hochman et al. |
| 6,560,975 | B1 | 5/2003 | Weldon |
| 8,535,275 | B2 | 9/2013 | Salzman |
| 8,535,276 | B2 | 9/2013 | Salzman |
| 2010/0022965 | A1 | 1/2010 | Salzman |
| 2010/0211010 | A1 | 8/2010 | Wycoki |
| 2011/0098634 | A1 | 4/2011 | Wycoki |
| 2011/0245769 | A1 | 10/2011 | Wycoki |
| 2014/0074025 | A1 | 3/2014 | Marti |

FOREIGN PATENT DOCUMENTS

| | | | |
|---|---|---|---|
| KR | 200473199 | Y1 | 6/2014 |
| WO | WO03024513 | | 3/2003 |
| WO | WO2011040900 | | 4/2011 |

METHOD AND APPARATUS FOR APPLYING AN ANESTHETIC AND BATERICIDE

PRIORITY CLAIM

In accordance with 37 C.F.R. 1.76, a claim of priority is included in an Application Data Sheet filed concurrently herewith. Accordingly, the present invention claims priority as a continuation-in-part of U.S. patent application Ser. No. 13,927,454, entitled "METHOD AND APPARATUS FOR APPLYING AN ANESTHETIC AND BACTERICIDE", filed Jun. 26, 2013, which is a continuation-in-part of U.S. patent application Ser. No. 12/557,753, entitled "METHOD AND APPARATUS FOR APPLYING AN ANESTHETIC", filed Sep. 11, 2009, now U.S. Pat. No. 8,500,678, issued Aug. 6, 2013, which is a continuation-in-part of U.S. application Ser. No. 11/636,859, entitled "DENTAL SYRINGE", filed on Dec. 11, 2006, now abandoned, which claims the priority to U.S. Provisional Patent Application No. 60/733,757, entitled "CRYO-SYRINGE", filed on Mar. 7, 2006. The contents of which the above referenced applications are incorporated herein by reference.

FIELD OF THE INVENTION

An apparatus for applying an anesthetic to a patient. In particular, the apparatus comprises a receptacle which is removably attached to a syringe barrel and which accommodates a container comprising an anesthetizing composition.

BACKGROUND

Syringes are employed millions of times daily all over the world to inject medicines into people as well as animals. Many times, injections are made in areas of the body that are somewhat less sensitive to pain. Other locations of the body where injections are contemplated are significantly more sensitive to pain and the patient feels a pinching sensation that may be quite painful as the syringe needle is inserted beneath the skin. Such areas include, for example, gums, areas of the face such as the forehead, as well as the lips. To minimize the pain that results when the injection needle penetrates, for example, a patient's gums, the dental practitioner will often apply a topical agent to the injection site using a cotton swab. Because the deadening agent is only applied topically, it is not effective as it does not cross the skin/mucosal membranes and misleads the patient into a false expectation of a painless injection. As a result, injecting an anesthetic often causes significant pain at the injection site.

SUMMARY

There is currently a need for a means of minimizing the pain associated with an anesthetic injection. The present invention addresses this need by providing a syringe having a liquid anesthetic, or a liquid anesthetic cartridge and a compressed gas or vapor canister therein, or a receptacle for receiving a gas or vapor canister, wherein the receptacle comprises a clip for attaching a syringe e.g. piggyback. One chamber within the syringe or syringe cartridge includes a conventional anesthetic while the canister includes a compressed, endothermic gas or vapor that rapidly absorbs heat when released to the atmosphere; the endothermic gas or vapor is first applied to the injection site prior to the anesthetic injection to minimize the pain associated with conventional anesthesia techniques. Furthermore, the gas or vapor also blanches the mucosa (along with popping bubbles due to the boiling of the liquid phase) allowing a practitioner to readily identify the pretreated injection site so that the needle is not inserted into an unanesthetized area.

Embodiments of the invention are also directed to an apparatus comprising a syringe, a receptacle which is removably attached to the syringe barrel and which accommodates a canister comprising a gaseous (vaporous) anesthetizing composition. The receptacle further comprises an elongated nozzle or a short nozzle for attaching a tube. The apparatus comprises an actuating member which acts to dispense the contents of a container or canister containing the anesthetic composition. The actuating member comprises a lever and a spring biased means for the controlled release of the gaseous (vaporous) anesthetizing composition.

Other aspects are described infra.

BRIEF DESCRIPTION OF THE DRAWINGS

FIG. 11B top view of the sleeve illustrated in FIG. 11A.

DETAILED DESCRIPTION

Figure 2:
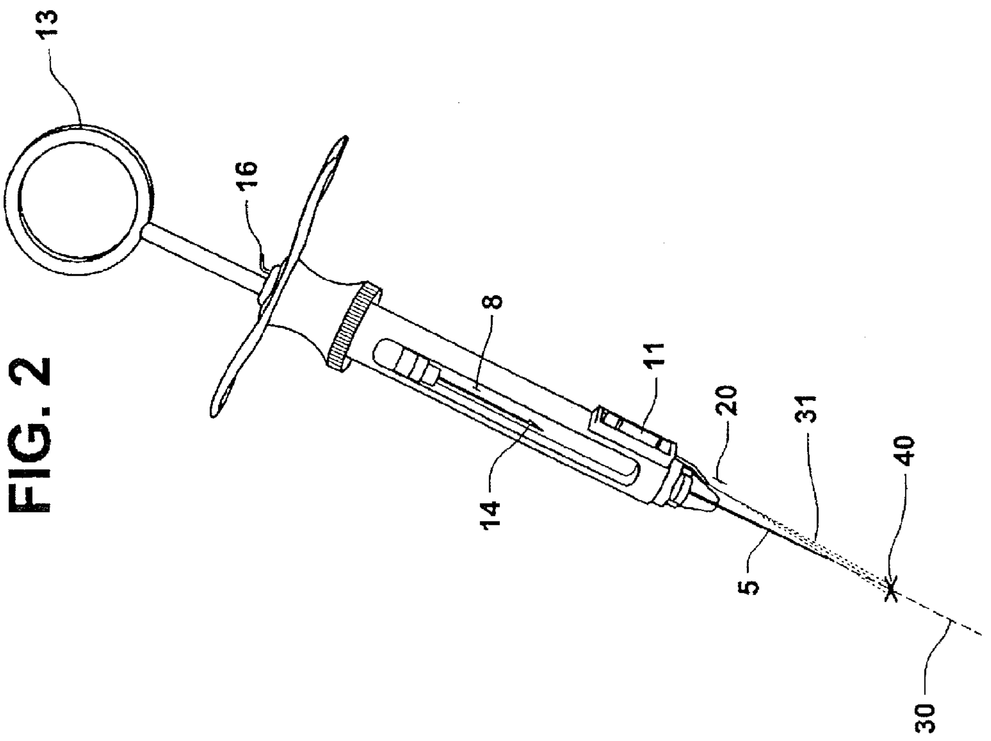
FIG. 2 is a plan view of the dental syringe with the cartridge and canister installed in their corresponding chambers.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

Referring to FIGS. 1-12, embodiments of the present invention relate to a method and apparatus of applying an anesthetic. In some embodiments, the apparatus comprises an elongated tubular housing 1 having an outer wall 2, an upper end 3, a substantially hollow interior, and a lower end 4 having an injection needle 5 extending therefrom. On the housing outer wall is an elongated opening 6 in communication with an anesthetic chamber 7 formed within the housing interior. The anesthetic chamber receives a cartridge 8 having a conventional dental anesthetic stored therein.

The outer wall also includes a smaller opening 9 that is in communication with an adjunctive chamber 10 for receiving a canister 11. The canister includes an endothermic gas (vapor) or "freeze spray" solution that rapidly absorbs heat when dispersed into the atmosphere.

Coaxially received within the anesthetic chamber is a plunger 12 having a thumb ring 13 at an upper end and a spear 14 at a lower end; the spear penetrates a membrane on the upper end of the anesthetic cartridge to force fluid therein into the injection needle.

Coaxially received within the adjunctive chamber is a depressible trigger 15 having a handle 16 at an upper end that protrudes from the upper end of the housing. Depressing the trigger opens the valve assembly 17 of the canister 11 propelling the gaseous or vaporous solution contained within canister 11 through an outlet nozzle 20 on the lower end of the housing. The nozzle 20 is oriented to project a stream of gas or vapor along a delivery axis 31 that intersects a delivery axis 30 of the needle, preferably at a point 40 immediately adjacent to the needle outlet. Accordingly, a practitioner can first deaden a proposed injection site and then immediately insert the needle with little movement or repositioning of the syringe.

The method of applying an anesthetic using the syringe described above includes initially dispersing the heat-absorbing, endothermic gas or vapor from the canister 11 onto a proposed injection site by depressing the trigger 15. Because of its physical properties, the heat-absorbing substance constricts blood flow at the injection site, and temporary numbing occurs. The freeze spray stops the propagation of the painful nerve stimuli and the patient feels the tactile or pressure as opposed to the pain sensation. The pressure nerve fibers supersede the painful nerve fibers so that the mechanical contraction of the muscles blocks the transmission of pain perception, according to the Gate theory. The use of the endothermic "freeze spray" also temporarily distracts the patient by creating a "popping" noise (due to the boiling of the liquid under pressure) that diverts the patient's attention away from any potential or anticipated pain. Finally, because the solution blanches the mucosa, a readily-visible target is created for insertion of the needle to assure that the deadened area is not bypassed. The aerosol propellants or gas (vapor) used as anesthetic herein, avoid the drawbacks associated with traditional anesthetics. The gas or vapor freezes (blanches) the area of administration allowing for the painless insertion of the needle to deliver the pharmaceutical drug, vaccine, BOTOX®, hair transplant and the like.

When the practitioner observes that the injection site mucosa has been blanched, the site is effectively deadened and a painless, concomitant injection is possible. The practitioner can then quickly inject the anesthetic into the blanched injection site by inserting the injection needle 5 and depressing the plunger 12. Because of the positioning of the gas or vapor outlet nozzle 20 and needle outlet 21, the dispersal of the gas or vapor and subsequent injection of anesthetic can be accomplished almost concurrently and with no pain to the patient.

Referring to FIGS. 3, 4A-C, 9A-C, 10A-F, 11A-D and 12A-E alternative embodiments of the present invention are illustrated. In these embodiments an apparatus comprising a module 44 which is removably attached to a syringe barrel 62 and which accommodates a canister 11 comprising a gaseous (vapor) anesthetizing composition. The module 44 includes an elongated outlet nozzle 20 for directing the gaseous (vapor) anesthetizing composition to intersect with the delivery axis 30 of the needle 5. The module includes an adjunct chamber frame 56, attachment means in the form of clips 23 or a sleeve 48, a trigger 15 and an outlet nozzle 20. The adjunct chamber frame 56 functions to contain the canister 11 as well as providing support for the trigger 15, clip(s) 23 and the dispenser cap 54. The trigger member 15 (FIG. 12A-E) functions to dispense the contents of the canister 11 containing the anesthetic composition by forcing the canister to slide within the adjunctive chamber 10 of the adjunct chamber frame 56. During the sliding action, the dispensing tube 58 of the canister 11 is pressed against the dispenser tube shoulder 55 to cause the canister valve 17 to open allowing compressed gas to escape through the dispenser tube 58. The trigger 15 is secured to the adjunct chamber frame 56 via pivot pins 60. The pivot pins 60 cooperate with pivot apertures 59 in the adjunct chamber frame 56. The pivot pins are positioned to allow the trigger to rotate thereabout so that the handle 16 can be utilized to force the ram 66 against the base of the canister 11 to cause the movement within the adjunctive chamber 10 to allow the pressurized gas to be released. A biasing means in the form of a spring 68 may be utilized to return the trigger to its original position. In some embodiments, the module 44 is disposable. In other embodiments, the syringe 42 is disposable. In yet other embodiments, the canister 11 is disposable. In other embodiments, any one or combination of parts of the apparatus is disposable.

Still referring to FIGS. 3, 4A-C, 9A-C, 10A-F, 11A-D and 12A-E, the module 44 includes an adjunctive chamber 10 for accepting a gas cartridge 8. The outer diameter of the module includes an attachment means which may comprise a clip 23 (FIG. 3) or sleeve 48 (FIG. 4A) which are adapted to cooperate with the outer diameter of a syringe barrel 62 for securing the module to the syringe. The clip 23 preferably includes a pair of arcuate members 24 made of a flexible resilient material so that the arcuate members may be temporarily enlarged by flexing to allow the arcuate members to snap over the outer diameter of the syringe barrel 62. In this manner, the module may be attached to syringe barrels of differing diameters to provide versatility to the device. The sleeve member 48 is also constructed from a flexible resilient material, such as plastic, and includes a slot 49 extending between two barrels 45, 47. In operation, the slot 49 may be expanded to allow the first and second barrels 45, 47 to be slipped over the outer diameter of the module 44 and the syringe 42. A fastener 51 may be provided to compress the slot 49 in the sleeve member 48 to prevent slippage of the assembly during use.

Figure 9A:
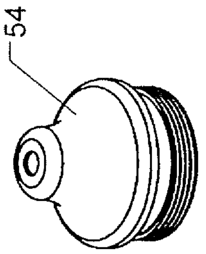
FIG. 9A is a perspective view of one embodiment of the dispenser cap of the present invention.
Figure 9B:
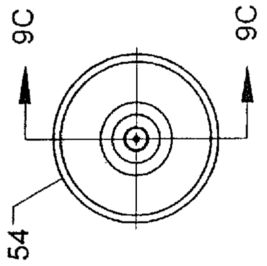
FIG. 9B is a front view of the dispenser cap illustrated in FIG. 9A.
Figure 9C:
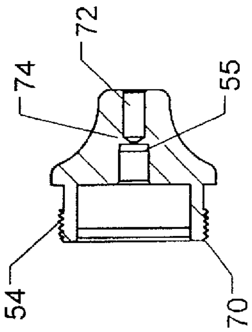
FIG. 9C is a section view taken along lines 9C-9C of FIG. 9B.
Figure 10F:
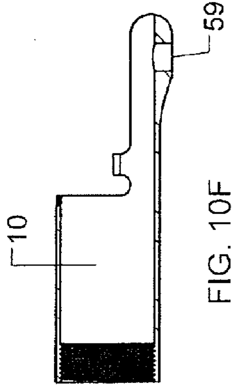
FIG. 10F is a section view of the adjunctive chamber taken along lines 10E-10F of FIG. 10E.
Figure 10E:
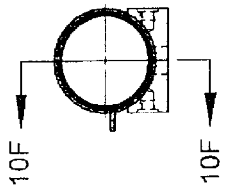
FIG. 10E is a top view of the adjunctive chamber illustrated in FIG. 10A.
Figure 10B:
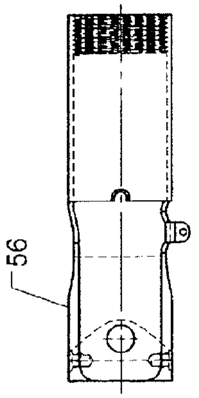
FIG. 10B is a front view of the adjunctive chamber illustrated in FIG. 10A.
Figure 10C:
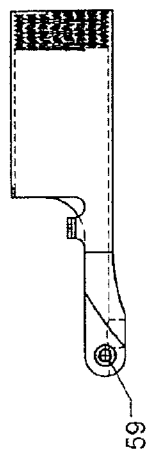
FIG. 10C is a side view of the adjunctive chamber illustrated in FIG. 10A.
Figure 10D:
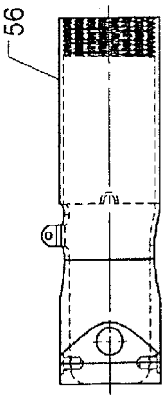
FIG. 10D is a rear view of the adjunctive chamber illustrated in FIG. 10A.
Figure 10A:
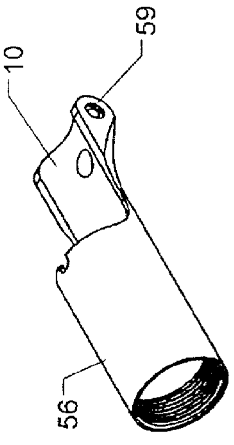
FIG. 10A illustrates one embodiment of an adjunctive chamber suitable for use with the present device.
Figure 11C:
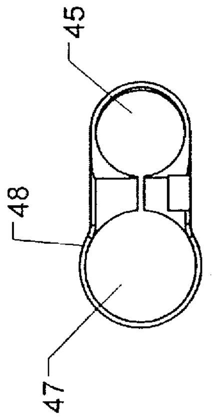
FIG. 11C bottom view of the sleeve illustrated in FIG. 11A with portions illustrated in phantom.
Figure 11D:
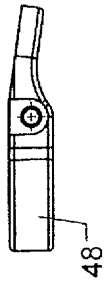
FIG. 11D front view of the sleeve illustrated in FIG. 11A.
Figure 11B:
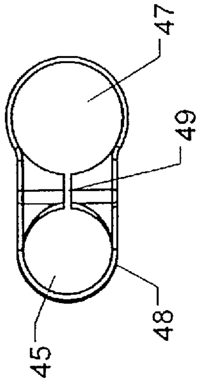
Figure 11A:
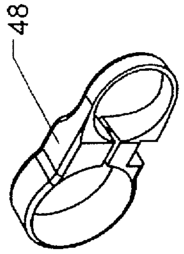
FIG. 11A is a perspective view of one embodiment of the sleeve of the present invention.
Figure 12D:
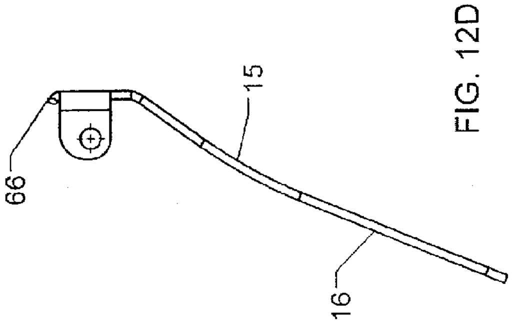
FIG. 12D is a right side view of the lever illustrated in FIG. 12A.
Figure 12E:
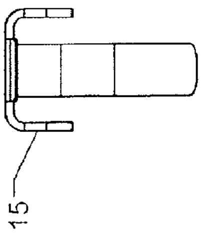
FIG. 12E is a top view of the lever illustrated in FIG. 12A.
Figure 12B:
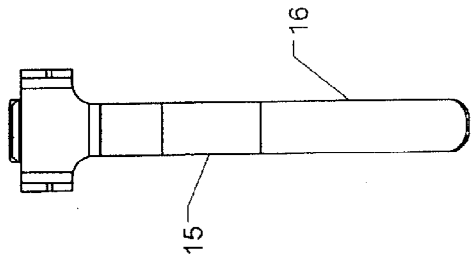
FIG. 12B is a top view of the lever illustrated in FIG. 12A.
Figure 12C:
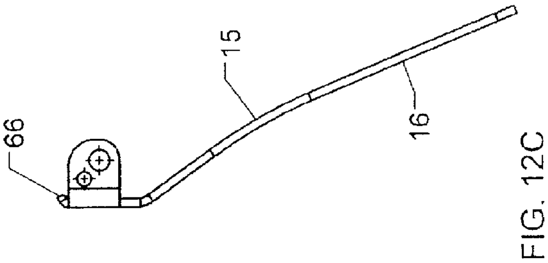
FIG. 12C is a left side view of the lever illustrated in FIG. 12A.
Figure 12A:
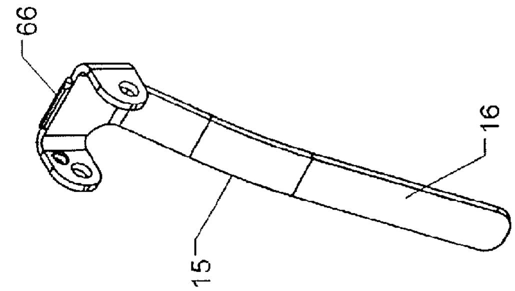
FIG. 12A is perspective view of one embodiment of the lever of the present invention.

Referring to FIGS. 9A-C, the dispenser cap is illustrated. The dispenser cap is used to close the end of the adjunct chamber frame 56 and to cooperate with the valve assembly 17 to cause the pressurized gas to be dispensed. In the preferred embodiment, the first end of the dispenser cap includes threads 70 which secure the dispenser cap to the adjunct chamber frame 56. Alternatively, adhesive, bayonet mount, friction fits or the like may be utilized to secure the dispenser cap to the adjunct chamber frame without departing from the scope of the invention. This is best seen in FIGS. 9 and 10 wherein the threaded cap 224 comprises an opening 27 and an engagement means, e.g. a valve 226 to engage the canister and for delivery of metered diseases of aerosol propellants. A restrictor jet 74 may be utilized to control the flow of gas through the outlet tube. The second end of the dispenser cap includes an outlet nozzle bore 72 sized to cooperate with the outlet nozzle 20 for positioning thereof. In the preferred embodiment, the outlet nozzle 20 is adhered or frictionally fit to the dispenser cap. The outlet nozzle 20 can be rigid, flexible or semi-flexible. The outlet nozzle 20 id tubular in construction having a distal end 51 with an opening 52 that may, if desired, be defined by an insert e.g. nozzle, venturi or the like, inserted into the opening 52 and having a particularly configured passageway, to cause the anesthetic sprayed therefrom to spray in a desired pattern. The distal end of the nozzle 20 can be flexible and may be bent by a physician into a desired angulation so that the anesthetic is sprayed in a desired location with respect to the location where the syringe needle will be inserted beneath the skin of the patient. The needle 5 can be varied in length, for example, shortened or elongated, so it extends beyond the distal termination of the outlet nozzle 20 so that the nozzle 20 doesn't interfere with insertion of the needle subcutaneously.

Figure 3:
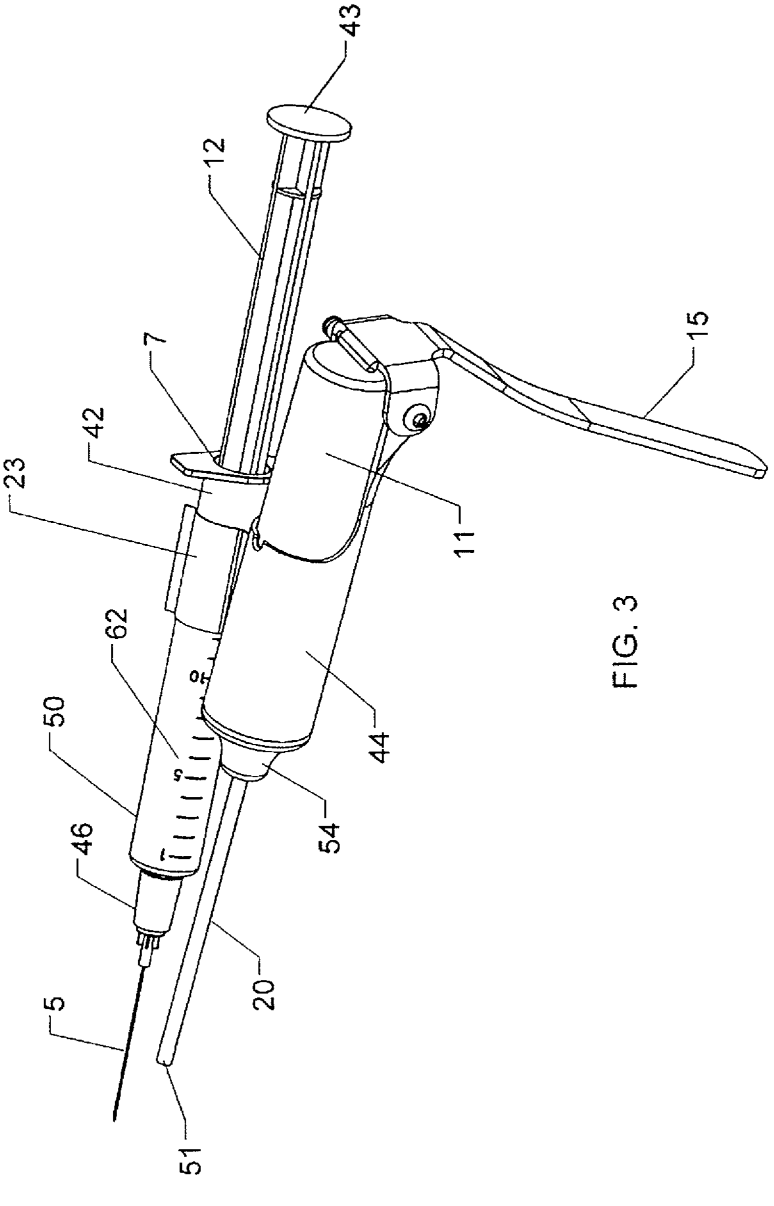
FIG. 3 is a perspective view illustrating an alternative embodiment of the present invention.
Figure 4B:
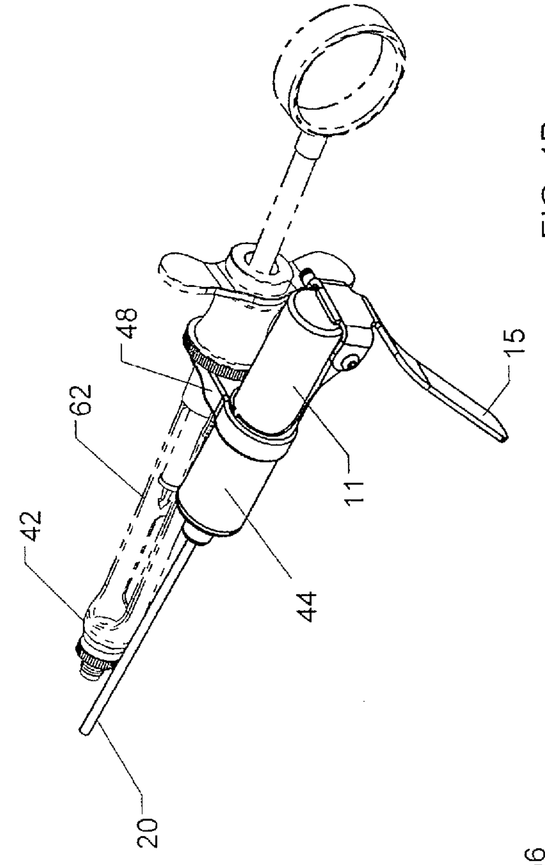
FIG. 4B is a perspective view of the embodiment illustrated in FIG. 4A attached to a syringe.
Figure 4A:
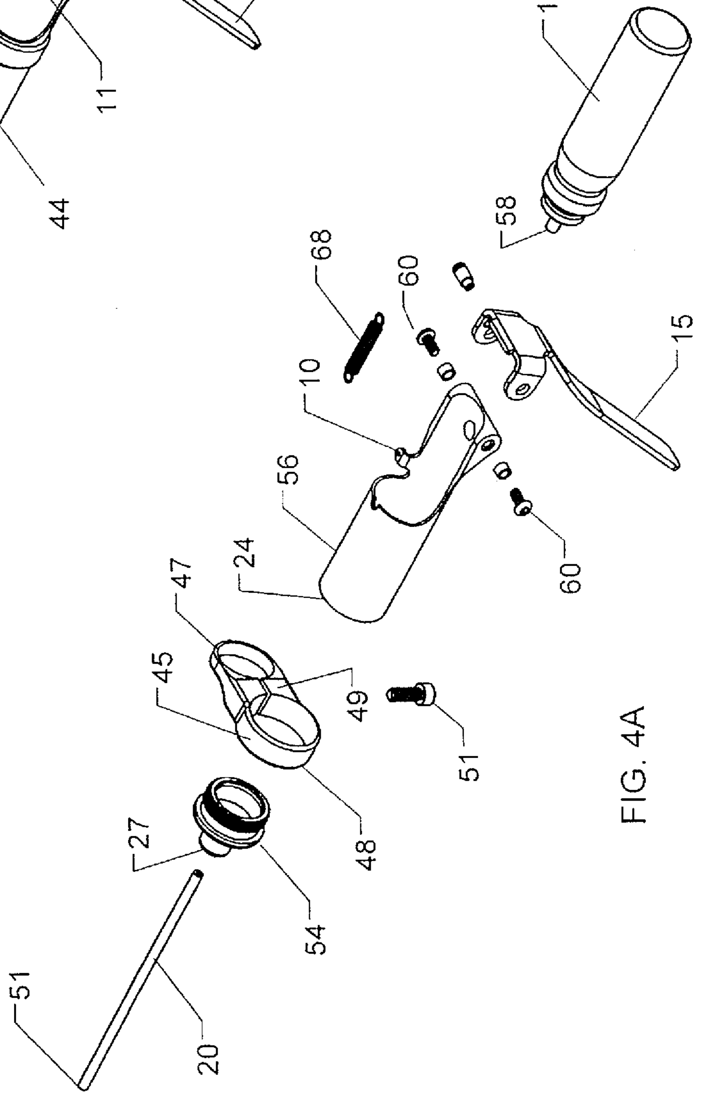
FIG. 4A is a plan view of one embodiment of a module of the present invention.
Figure 4C:
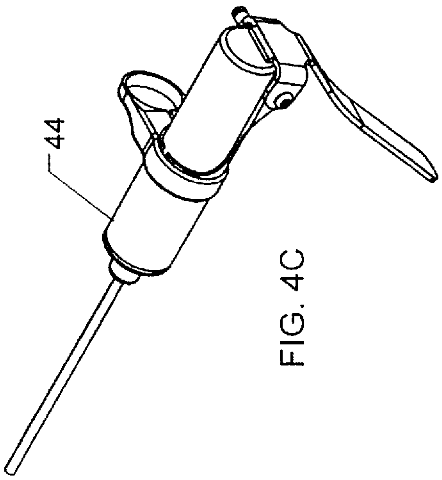
FIG. 4C is a perspective view of the module of FIG. 4A.
Figure 4D:
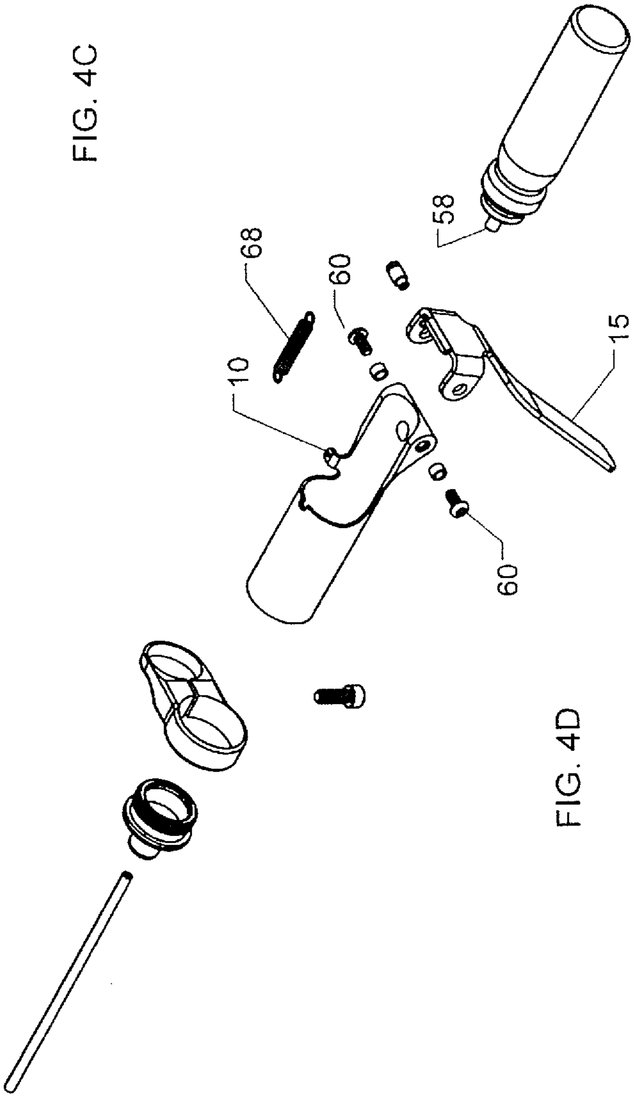
FIG. 4D is an exploded of the module of FIG. 4A.

As shown in FIG. 3, a disposable syringe 42 is illustrated in conjunction with the module of the present invention. The disposable syringe includes an elongated barrel 62 that is typically cylindrical in outer configuration, a plunger 12 having a thumb pad 43 or ring 13 (FIG. 1) that is engaged by the thumb or finger of the user, and a perpendicular tab 61 on the barrel 62 of the syringe 42 that is grasped by other fingers of the user while the ring or pad 13 is being pushed to cause the plunger 12 to move in a direction toward the distal end 50 of the barrel 62. The plunger 12 pushes the medicament or liquid in the chamber 7 through the needle. The needle 5 is attached to the distal end of the syringe via, locking taper, luer lock 46 or the like to allow fluid to flow into and through the needle 5. As is well known, the needle is thin and hollow permitting the medicament within the chamber 7 to be dispensed therethrough. The needle 5 can be of any length so long as its distal end extends beyond the end of outlet nozzle 20.

In the various embodiments, the anesthetic comprises one or more gas or vapor or aerosol propellants. These propellants can be any type of aerosol propellants as long as they continue to decrease the temperature of the patient's skin or mucosal area targeted for an injection. Examples are the aerosol propellants sold by DuPont Company, Wilmington, Del., under the trade names DYMEL™ 134a and DYMEL™ 227a. In preferred embodiments, the anesthetic comprises a blend of two aerosol propellants in varying percentages of weight/weight (w/w). The range of DYMEL™ 134a can be from about 0.001% to 99.999% w/w and the weight of DYMEL™ 227a can be from about 0.001% to 99.999% w/w. In other embodiments, one or more compounds, pharmaceutical grade compounds or compositions can be included; for example, compounds which alter the vapor pressure of the gas or vapor being emitted. Pharmaceutical compounds include, for example, antimicrobial, taste altering compounds or flavoring compounds, e.g. menthol, mint, etc., therapeutically effective compounds and the like. In preferred embodiments, the aerosol propellants (e.g. DYMEL™ 134a, DYMEL™ 227a) are pharmaceutical grade and shown to be safe for inhalation, ingestion, and for use in sensitive areas of a patient, e.g. eyes, lips, nose etc. These pharmaceutical grade aerosol propellants can be obtained from DuPont Company, Wilmington, Del.

The anesthetic is preferably contained within a small or specialized canister of the type typically utilized for metered dose inhalers (e.g., asthma) and includes a deep drawn metal canister constructed from a metal such as aluminum or steel. The deep drawn canister (FIG. 4D) includes a valve assembly 17 crimped and sealed within the open end of the metal canister to create a sealed pressure canister that is light weight and portable. The aerosol propellants are contained within the metal canister under pressure so that depression of the dispenser tube 58 releases the propellant through the valve assembly. In operation, the dispenser tube 58 of the valve assembly 17 may be operated in a variety of manners which may include, but should not be limited to, finger nozzles, levers, cams, solenoids or the like which permit the valve to be depressed for release of the propellant.

The location on the surface area of the patient where an injection is to take place is determined and the syringe 42 with the module 44 attached thereto is positioned at a desired location and angle of skin penetration approximately 1 to 2 centimeters above the skin. The lever 15 is depressed to engage the valve to permit flow of the anesthetic, e.g. an aerosol propellant (vapo-coolant), for a period of time, such as 1 to 3 seconds. Either while the aerosol propellant is flowing or just after the flow of the aerosol propellant is stopped, the skin is then penetrated by the needle of the syringe 5 to a desired depth and the medicament is injected to numb in a separate location, one at a time. Injections may be first, subcutaneous, then intramuscular or intradermal.

Figure 5A:
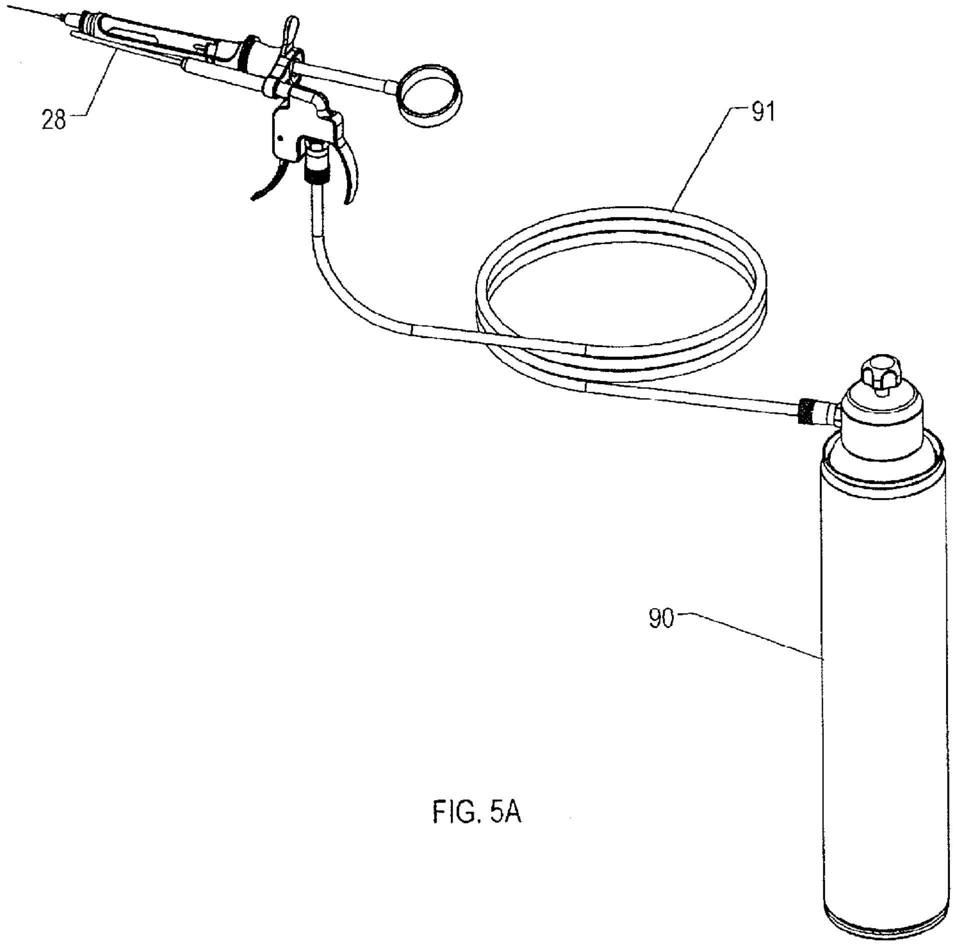
FIG. 5A is a perspective assembly view illustrating an alternative embodiment of the present invention having a remote tank for holding an endothermic gas or vapor.
Figure 5B:
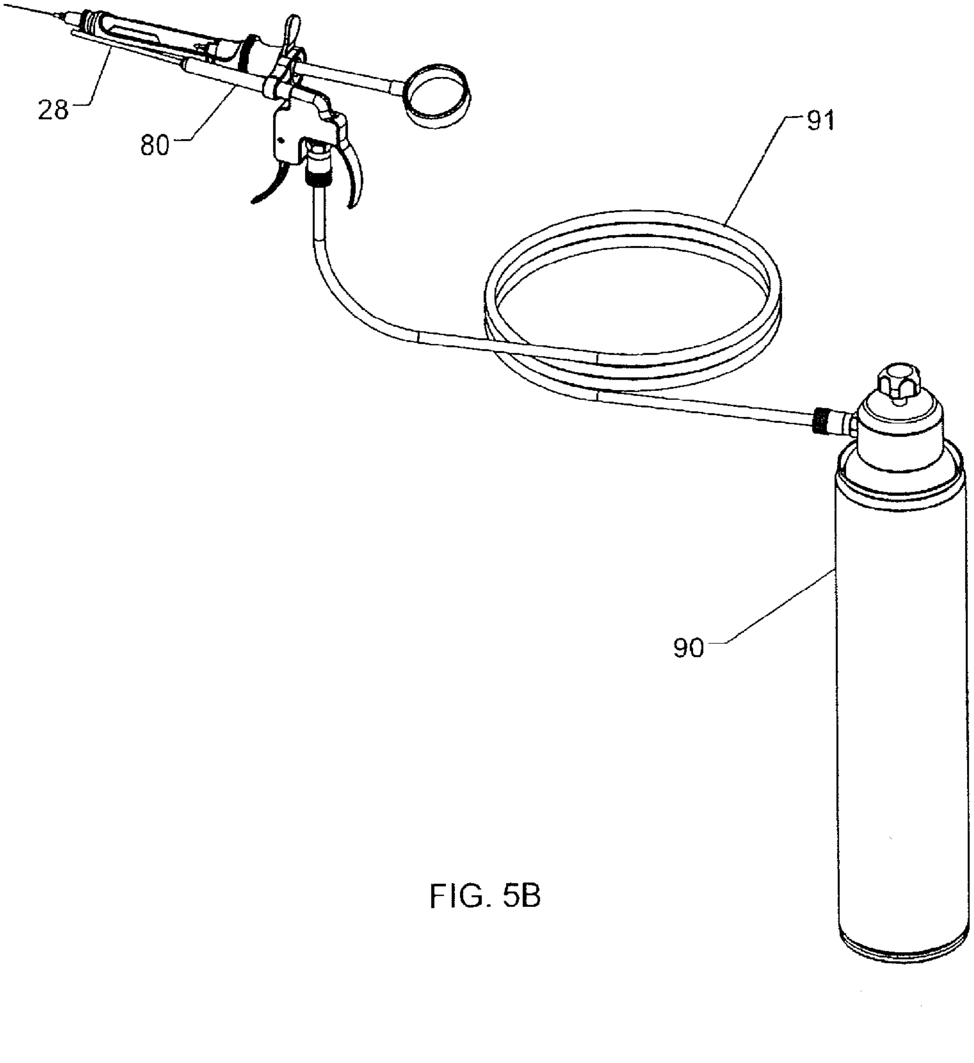
FIG. 5B is a perspective assembly view illustrating an alternative embodiment of the present invention having a remote tank for holding an endothermic gas or vapor.
Figure 5C:
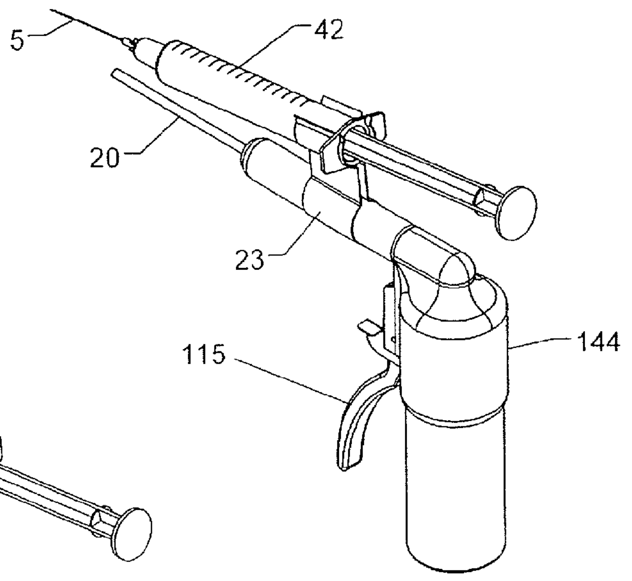
FIG. 5C is a perspective view of an alternative embodiment of the present invention.
Figure 5D:
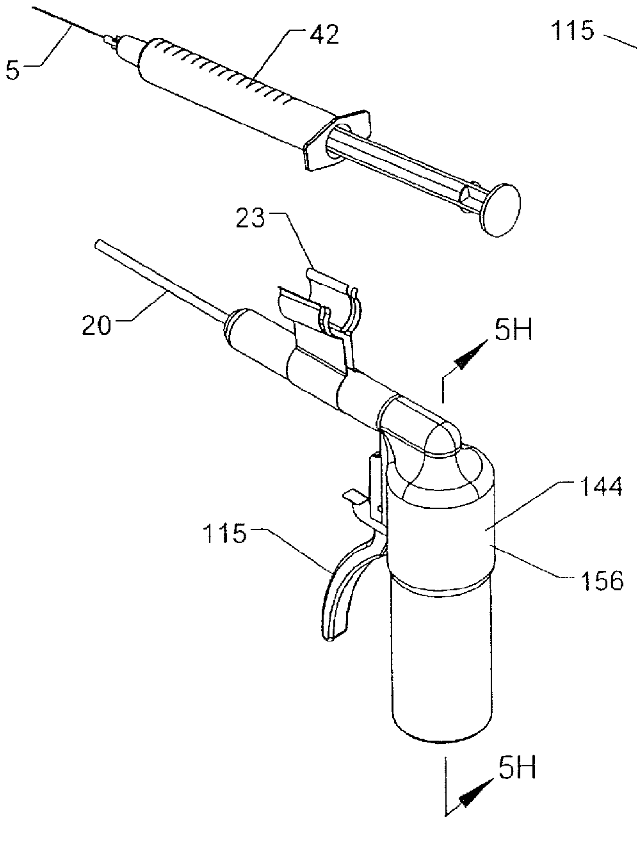
FIG. 5D is a partially exploded view of the embodiment illustrated in FIG. 5C.
Figure 5E:
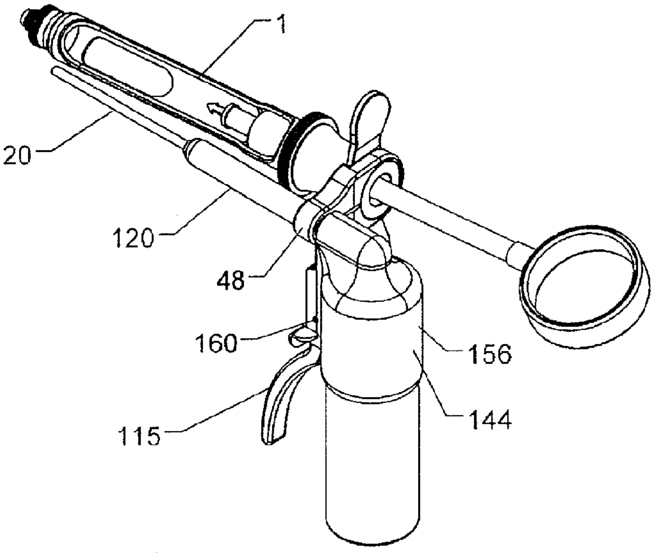
FIG. 5E is a perspective view of an alternative embodiment of the present invention.
Figure 5F:
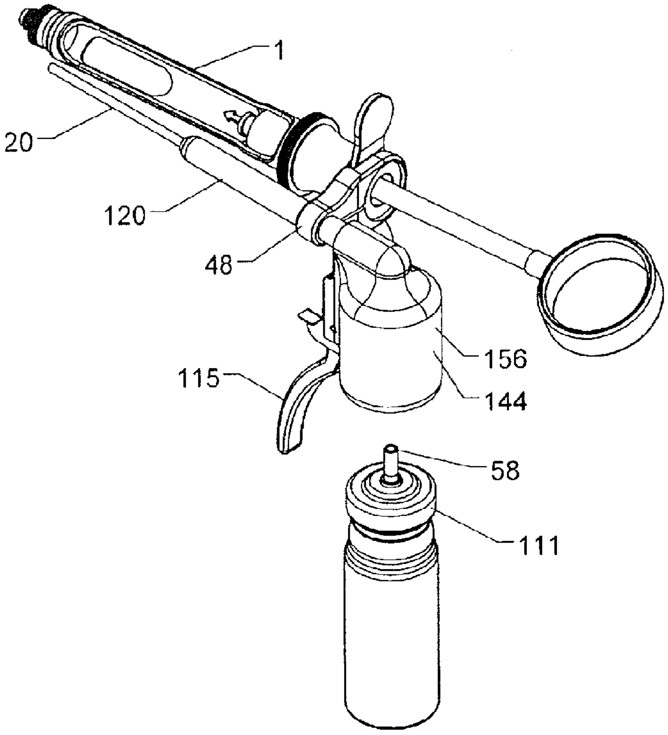
FIG. 5F is a partially exploded view of the embodiment illustrated in FIG. 5E.
Figure 5G:
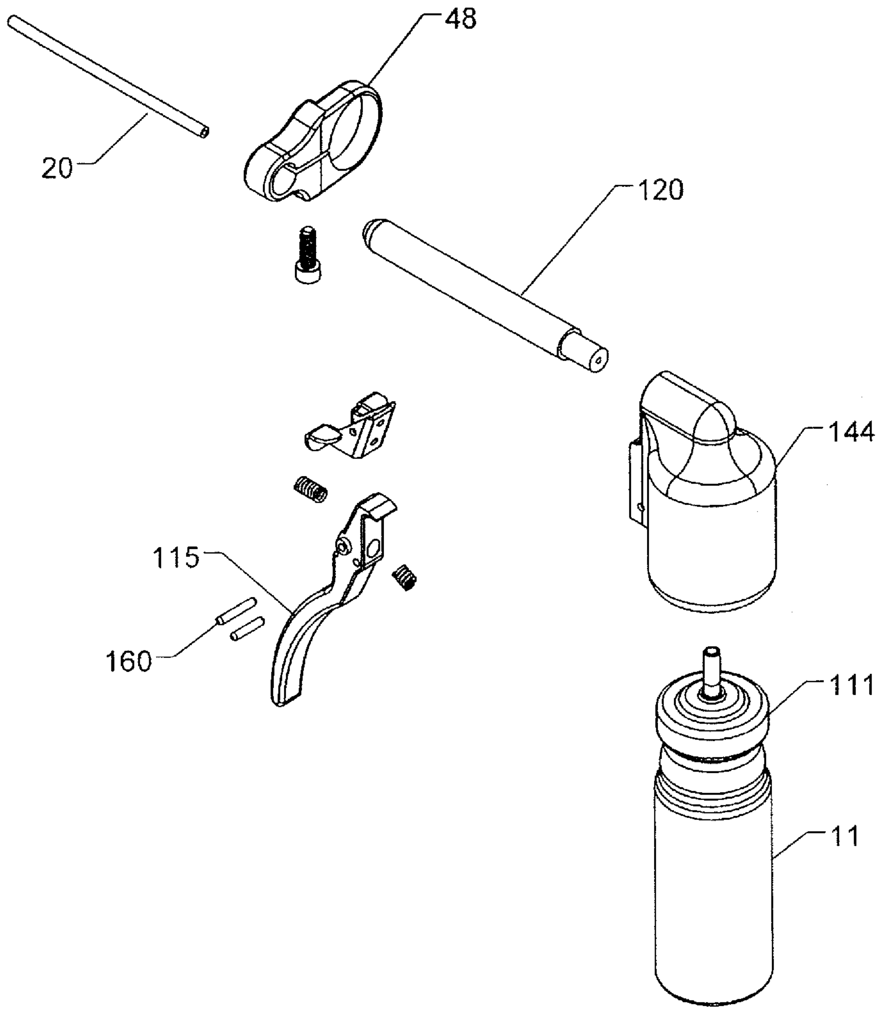
FIG. 5G is an exploded view of the embodiment illustrated in FIG. 5G.
Figure 5H:
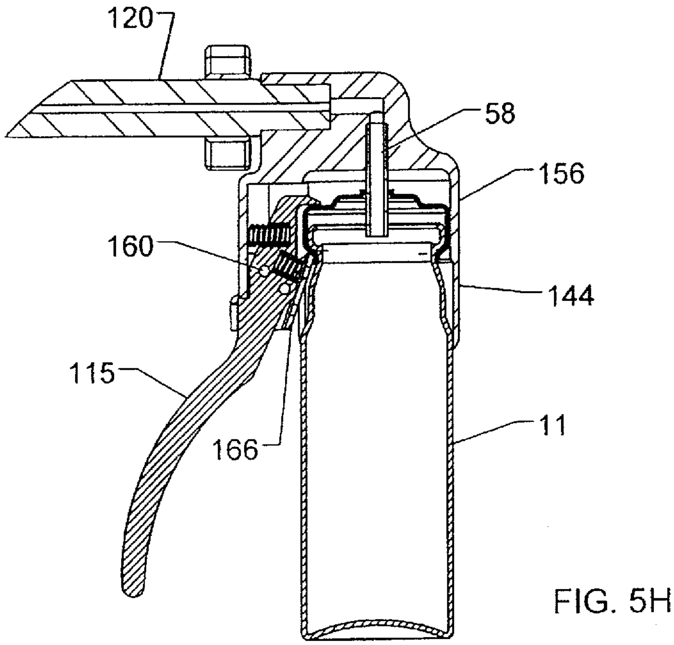
FIG. 5H is a section view taken along lines 5H-5H of FIG. 5D.
Figure 5I:
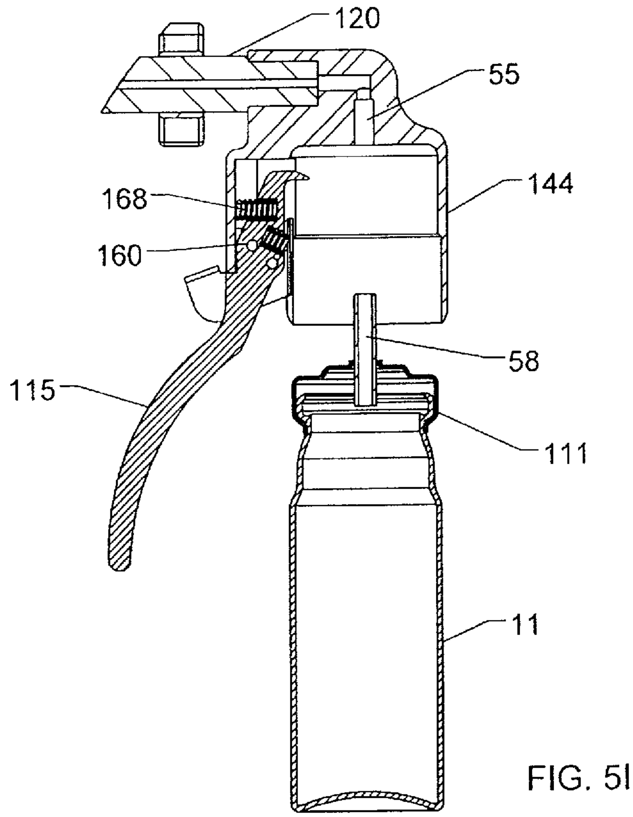
FIG. 5I is a partially exploded view of the embodiment illustrated in FIG. 5H.
Figure 5J:
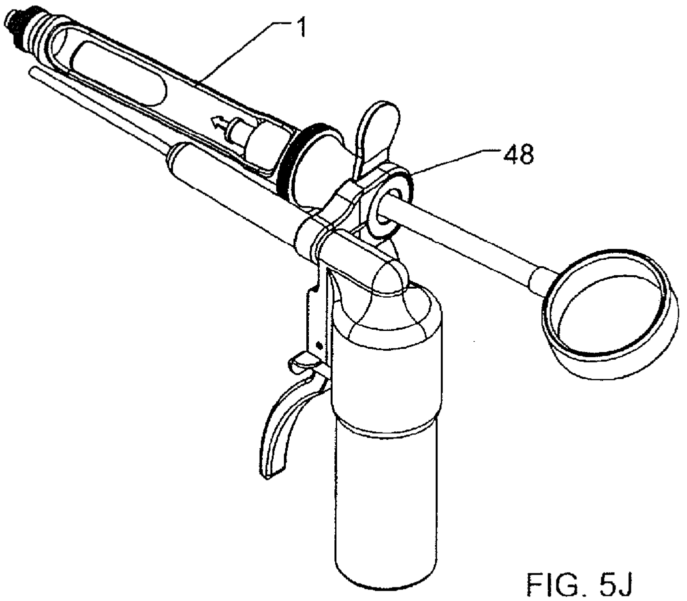
FIG. 5J is a perspective view of an alternative embodiment of the present invention.
Figure 5K:
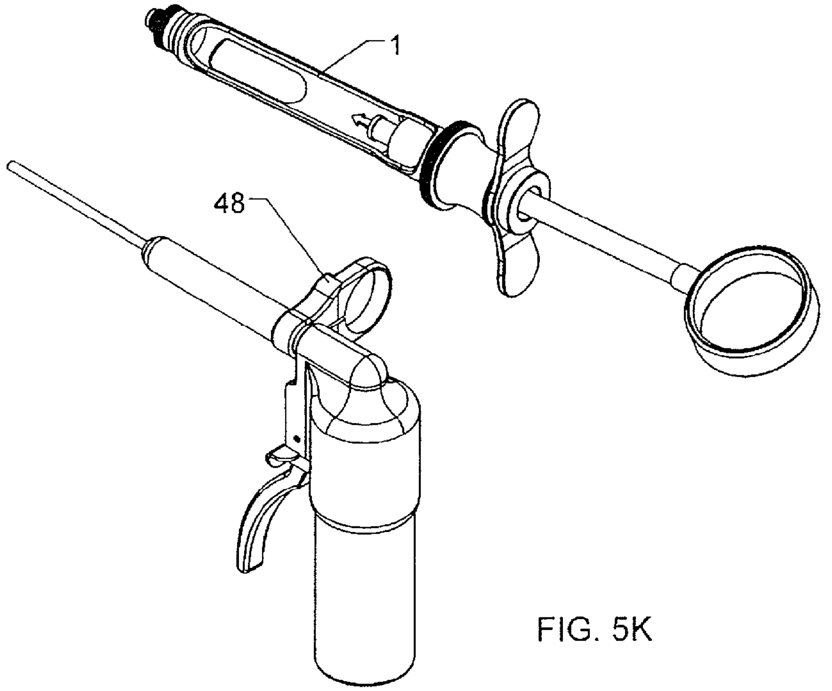
FIG. 5K is a partially exploded view of the embodiment illustrated in FIG. 5J.

The anesthetic can be administered at various depths in sequence of the dermal layers to make sure that the area is numb, such that a patient will not feel any pain when the needle, e.g. i.v. injection is inserted. In some embodiments, the first dermal or skin layer is numbed first, and then the next layer etc., in sequence. If desired, the needle may be retracted a desired distance with additional injection occurring or may be removed so that the next location can be chosen. During the step-wise process of injection including multiple injections at the same site of needle penetration, additional aerosol propellants may be dispensed as desired to maintain the numbness of the skin at that location. If during the process of injection, the canister 11 runs out of anesthetic, e.g. an aerosol propellant, it may be removed from the adjunct chamber frame 56 and replaced with a replacement canister. In embodiments where a large area is targeted for numbing, a larger volume or quantity of aerosol propellant in a large canister 90 can be carried so as not to contaminate the field or location and to prevent cross contamination (FIGS. 5A, 5B). In some embodiments, the apparatus comprises an assembly which is attachable to a user's clothes or belts, or a back-pack carrying any further number of doses of propellant. In this manner, the user is not required to replace a spent canister. The assembly is connected to the remote valve assembly 80 via a long flexible tube 91 which can be extended or retracted as needed by the user, and is actuated in a similar manner as with the smaller canister 11 or the tube is connected to the canister thereby providing a reservoir of aerosol propellant. The canister may also be refillable and may additionally include regulators or the like known in the art for reducing pressure from large high pressure tanks. When the injection process is completed, the syringe 42 may be removed from the clip portion 23 and suitably discarded and the module 44 may be re-used with other syringes or for single use per point to prevent cross-contamination. It should also be noted that while the preferred embodiment entails placing the large canister in a fixed position, the canister may optionally include an attachment means for securing the canister to the belt or back of the user to provide mobility to the user while still providing the added capacity of the larger canister.

As such, in this way, the present invention provides an effective way of dispensing an anesthetic onto the skin of a patient where an injection is to take place so that the injection is painless. The present invention is not limited for use in association with injections in the face for aesthetic enhancement. Rather, it may be used as an attachment to any syringe or other injection device used to inject any medication for any purpose. For example, the inventive device may be used with injection devices associated with diabetes glucose monitors, BOTOX®, hair transplants, multiple needle allergy introducers and the like.

Figure 1:
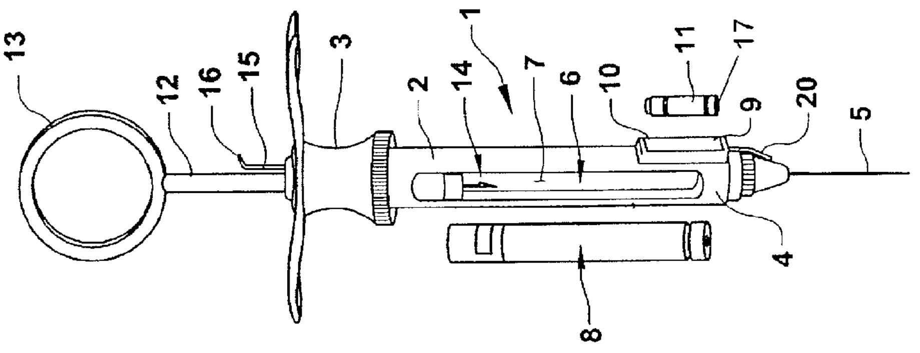
FIG. 1 is a plan view of the dental syringe with the cartridge and canister removed therefrom.

Referring to FIGS. 1 and 2, the apparatus comprises an elongated tubular housing 1 having an outer wall 2, an upper end 3, a substantially hollow interior, and a lower end 4 having an injection needle 5 extending therefrom (FIGS. 1, 2). On the housing outer wall is an elongated opening 6 (in communication with an anesthetic chamber 7 formed within the housing interior. The anesthetic chamber receives a cartridge 8 having a conventional dental anesthetic stored therein.

The outer wall can also include a smaller opening 9 (FIG. 1). The receptacle or adjunctive chamber 10 for receiving a canister 11 (FIG. 2). The canister includes an endothermic gas or vapor or "freeze spray" solution that rapidly absorbs heat when dispersed into the atmosphere. Coaxially received within the anesthetic chamber is a plunger 12 having a thumb ring 13 or other means for pushing the plunger at an upper end.

Coaxially received within the adjunctive chamber is a depressible trigger 15 having a handle 16 at an upper end that protrudes from the upper end of the housing. Depressing the trigger propels the gaseous or vapor propellant through an outlet nozzle 20 on the lower end of the housing. The nozzle 20 is oriented to project a stream of gas or vapor along a delivery axis that intersects a delivery axis of the needle, preferably at a point immediately adjacent to the needle outlet. Accordingly, a practitioner can first deaden a proposed injection site and then immediately insert the needle with little movement or repositioning of the syringe.

Figure 6:
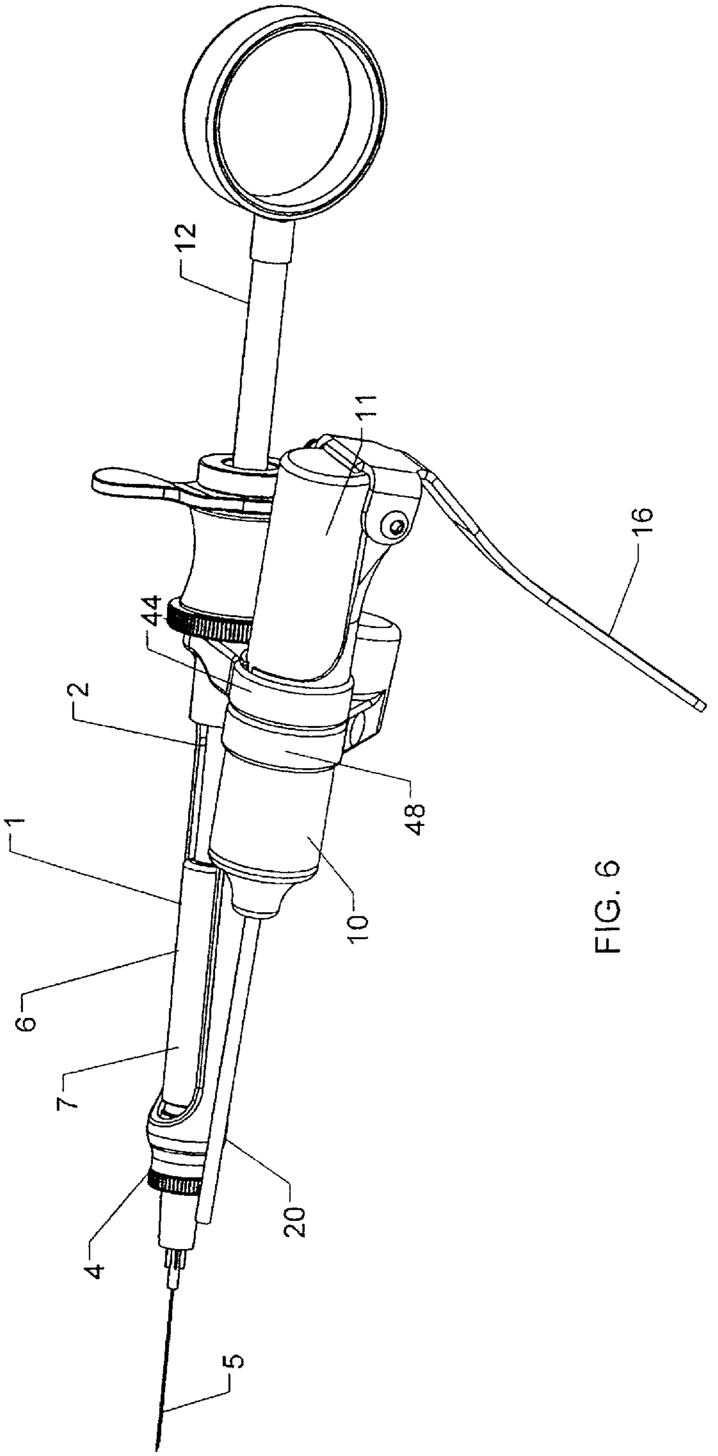
FIG. 6 is a plan view of a syringe with the canister installed in the module or adjunctive chamber.
Figure 7:
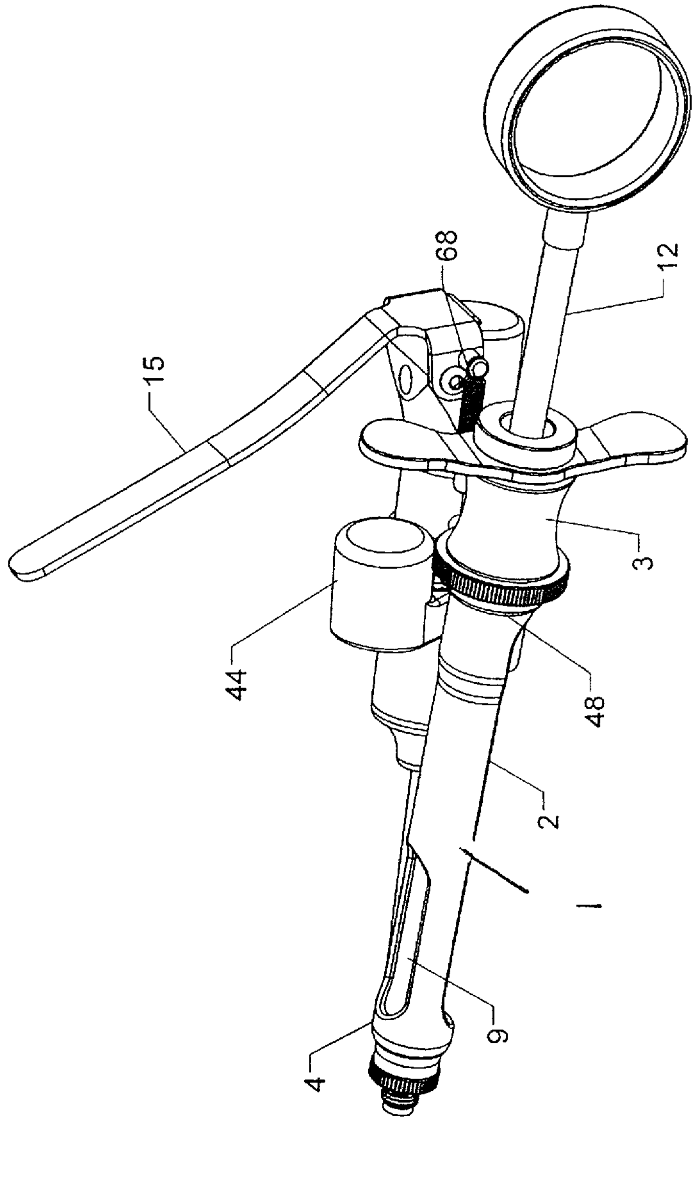
FIG. 7 is a perspective view of the embodiment illustrated in FIG. 6.
Figure 8:
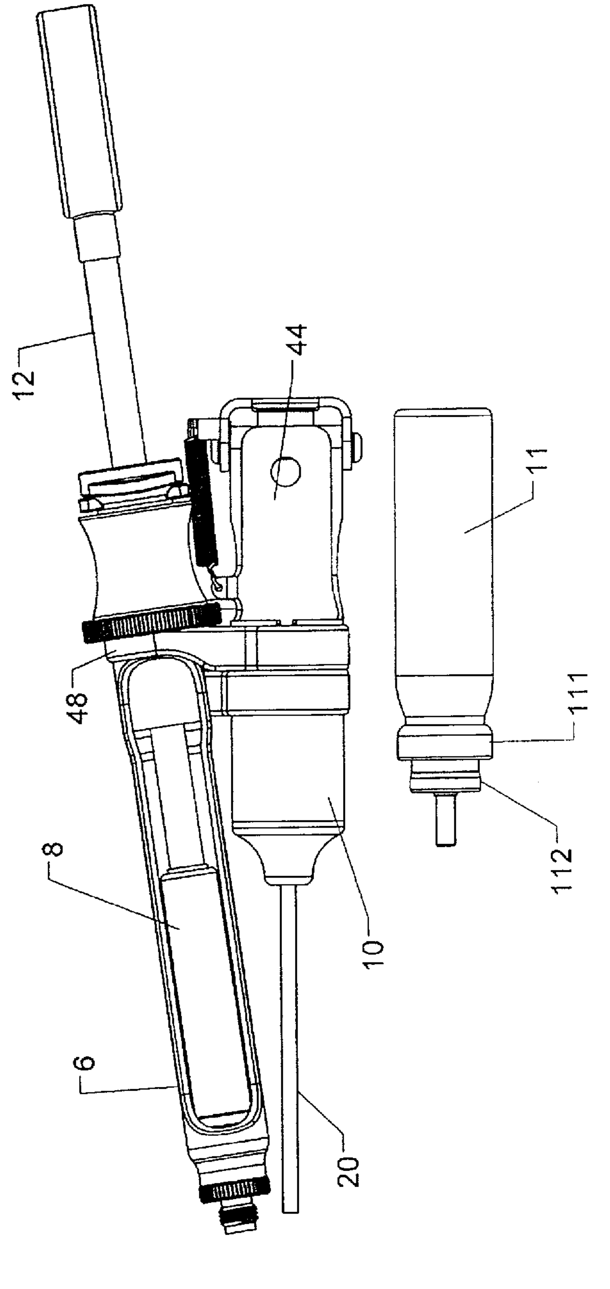
FIG. 8 is a partially exploded front view of the embodiment illustrated in FIG. 6.

Referring to FIGS. 6-8, an alternative embodiment of the present device is illustrated. This embodiment utilizes a reusable syringe in combination with the Module 44 and the sleeve 48 for attaching the module to the syringe. This embodiment also illustrates that the module and the sleeve may be constructed from metal without departing from the scope of the invention.

In some embodiments, the module 44 may be constructed and arranged to accommodate two or more canisters 11. The arrangement of the two or more canisters or modules can be arranged in any manner and can be of varying dimensions and shapes. For example, the modules can be attached together. In some embodiments, the modules 44 are arranged to be on either side of the syringe. One of ordinary skill in the art can envisage possible combinations, locations, patterns and designs for the receptacles.

Referring to FIG. 8, the container or canister 11 which contains one or more gases or vapors comprises a neck 111 having an end cap 112 and a dispenser tube 58 dimensioned for slidable insertion and engagement of the dispenser cap 54 of the module 44 (FIG. 8). The canister contents can be any type of anesthetic. In embodiments, the anesthetic comprises one or more gases (vapors). Examples include, without limitation, aerosol propellants, endothermic gases (vapors) that rapidly absorb heat when released to the atmosphere and the like. Accordingly, a user can initially disperse the gas or vapor composition onto the injection site to minimize any pain and discomfort associated with an injection. Subsequently, the practitioner inserts the needle into the deadened site (blanched) and injects the contents of the syringe. As discussed above, the receptacle can be of any size and shape to accommodate canisters or containers of varying sizes and shapes. The size of the canisters used depends on the volume of the anesthetic, e.g. gas or vapor needed for the particular procedure. Different blends produce different temperatures; therefore, the doctor in charge can decide which of the blends to utilize for the necessary effect. In some embodiments, the temperature of the gas or vapor when administered is above freezing temperature to avoid necrosis, frost bite, pain, discomfort or any type of biological damage to the area of administration. Since the medical caregiver, e.g. doctor, controls the delivery of the anesthetic, e.g. gas or vapor, the doctor is in charge of the delivery of the gas or vapor to enhance the patient comfort, therefore, the doctor can add additional bursts if the patient informs the doctor that more is needed.

Referring to FIGS. 5C-K, an alternative embodiment of the present invention is illustrated. In this embodiment, the module 144 is constructed and arranged to be secured to the syringe 42 in a perpendicular arrangement with respect to the syringe. The adjunct chamber frame 156 is still constructed to allow the insertion of a portion of the canister 11. The distal end of the adjunct chamber frame 156 includes the dispenser tube shoulder 55 for accepting the dispenser tube 58. In this embodiment, the trigger 115 is constructed and arranged to cooperate with the neck 111 of the canister 11 to provide controlled dispensing of the pressurized gas. The trigger 115 is provided with a pivot pin 160 which allows the ram 166 to catch under the neck to cause the canister to move within the adjunct chamber frame. Return spring 168 returns the trigger to its original position. An outlet tube 120 extends out of the adjunct chamber frame 156 at an angle that is substantially perpendicular with respect to the canister 11. The outlet tube 120 therefore provides a body to cooperate with the sleeve 48 or clip 23 for ready attachment to reusable or disposable syringes. The outlet tube also functions to secure and position the outlet nozzle 20 which may be telescopingly engaged to the outlet tube to allow the length of the outlet nozzle to be adjusted.

It should also be noted that while not shown, a small laser light or the like may be secured to the module 44, 144 to indicate the trajectory of the pressurized gas. In this manner, the user would be provided with a visual guide to where the gas will strike the patients skin.

The above-described device is not limited to the exact details of construction and enumeration of parts provided herein. For example, the receptacle could comprise separate components, e.g. a separate clip that is attachable to the receptacle and to any conventional syringe. The endothermic gas or vapor should remove sufficient heat to function as described without causing necrosis. The concentration and volume of the propellant components can be varied to deliver small doses of highly-concentrated substances, or a prolonged, continuous dispersal of diluted substances. The canister can also be color coded for varying temperatures produced by the different blends or aerosol propellants. In addition, gas or vapor delivery can be automated with a laser mechanism that dispenses gas or vapor when the needle is within a minimal distance from the skin and automatically disables gas or vapor flow upon needle penetration. Accordingly, a practitioner can rapidly inject multiple sites. Finally, although the device has been primarily described and depicted as a syringe, the gas or vaporous canister could have other uses. For example, it could be attached to a scalpel blade to allow a quick, painless incision when performing certain procedures, such as removing moles. Furthermore, the size, shape and materials of construction of the various components can be varied.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An injection apparatus comprising: a syringe, said syringe including an outer wall having a hollow interior, an upper end and a lower end, an injection needle extending from said lower end, a plunger received in said hollow interior for forcing liquid from said hollow interior through said injection needle, an adjunctive chamber sized to receive a canister, said adjunctive chamber attached to said syringe, said canister having a compressed endothermic gas therein, an actuating member for dispensing contents from the canister, and an outlet nozzle for dispensing contents from said canister along a delivery axis that intersects a delivery axis of said injection needle.

2. The injection apparatus of claim 1, wherein said compressed endothermic gas in the canister is dispensed when a user operates means for dispensing said compressed endothermic gas through said outlet nozzle.

3. The syringe assembly of claim 1, wherein said canister containing a compressed endothermic gas includes a valve, an actuating member is connected to the valve for dispensing the contents of the canister through the nozzle, the contents of canister being sprayed from the nozzle topically onto a skin surface.

4. The syringe assembly of claim 1, wherein a nozzle trajectory is along a delivery axis that intersects a delivery axis of said needle positioned on said syringe.

5. A syringe comprising: an elongated tubular housing having an outer wall, a substantially hollow interior, an upper end and a lower end; an injection needle extending from the lower end of the housing; an adjunctive chamber or receptacle secured to said tubular housing; a canister received within said adjunctive chamber or receptacle, said canister having a compressed, endothermic gas or vapor therein that rapidly absorbs heat when released to the atmosphere; means for dispensing a pharmaceutical composition through said injection needle; an outlet nozzle in fluid communication with said canister; means for dispensing said gas or vapor through an outlet nozzle.

6. The syringe according to claim 5, wherein said means for dispensing said pharmaceutical composition through said needle comprises: said pharmaceutical composition in said hollow interior being in fluid communication with said needle; a plunger received within said hollow interior that, when depressed, forces the pharmaceutical composition from said hollow interior into said needle.

7. The syringe according to claim 5, wherein said nozzle is oriented to project said gas or vapor along a delivery axis that intersects a delivery axis of the needle allowing said gas or vapor and said pharmaceutical composition to be successively delivered to an injection site with minimal repositioning of the housing.

* * * * *